US010912939B2

(12) United States Patent
Lebreton et al.

(10) Patent No.: US 10,912,939 B2
(45) Date of Patent: Feb. 9, 2021

(54) ELECTROPORATION DEVICE

(71) Applicant: EYEVENSYS, Paris (FR)

(72) Inventors: Luc Lebreton, Paris (FR); Elodie Touchard, Le Mans (FR); Romain Benard, Paris (FR); Karine Bigot, Lunay (FR); Cécile Madaras, Saint-Maur (FR); Francine Behar-Cohen, Saint-Sulpice (CH)

(73) Assignee: EYEVENSYS, Paris (FR)

( * ) Notice: Subject to any disclaimer, the term of this patent is extended or adjusted under 35 U.S.C. 154(b) by 505 days.

(21) Appl. No.: 15/567,002

(22) PCT Filed: Apr. 13, 2016

(86) PCT No.: PCT/EP2016/058138
§ 371 (c)(1),
(2) Date: Oct. 16, 2017

(87) PCT Pub. No.: WO2016/166172
PCT Pub. Date: Oct. 20, 2016

(65) Prior Publication Data
US 2018/0289958 A1 Oct. 11, 2018

(30) Foreign Application Priority Data
Apr. 14, 2015 (EP) .................................. 15305548

(51) Int. Cl.
*A61N 1/32* (2006.01)
*A61F 9/00* (2006.01)
(Continued)

(52) U.S. Cl.
CPC ............ *A61N 1/327* (2013.01); *A61F 9/0008* (2013.01); *A61F 9/0017* (2013.01); *A61M 5/32* (2013.01);
(Continued)

(58) Field of Classification Search
CPC .................................. A61M 5/46; A61N 1/327
See application file for complete search history.

(56) References Cited

U.S. PATENT DOCUMENTS

| 2011/0152749 A1* | 6/2011 | Touchard | .............. | A61F 9/0008 604/21 |
| 2012/0232522 A1 | 9/2012 | Prausnitz et al. | | |
| 2014/0107559 A1 | 4/2014 | Roy | | |

FOREIGN PATENT DOCUMENTS

| EP | 2 767 307 A1 | 8/2014 | | |
| EP | 2767307 A1 * | 8/2014 | ............. | A61N 1/327 |

(Continued)

OTHER PUBLICATIONS

U.S. Appl. No. 12/921,979, filed Jan. 24, 2011 in the name of Elodie Touchard et al.

(Continued)

Primary Examiner — Nathan R Price
Assistant Examiner — Melissa A Snyder
(74) Attorney, Agent, or Firm — Oliff PLC

(57) ABSTRACT

An electroporation device for injecting a product into a ciliary muscle of an eye, said device comprising: a support having a support contact surface extending along a virtual sphere having a radius between 10 and 15 mm, so as to match the outside surface of the eye, a first electrode comprising an invasive electrode needle, a second electrode having an electrically conductive electrode contact surface, optionally an injection needle, wherein the support comprises an insertion guide configured to guide a sliding of said electrode needle and/or injection needle along a respective insertion axis, so that the angle between said insertion axis and a plane tangential to the virtual sphere at the insertion point is less than 40°, the insertion point being the point where said insertion axis crosses said virtual sphere.

28 Claims, 6 Drawing Sheets

(51) Int. Cl.
*A61M 5/32* (2006.01)
*A61N 1/05* (2006.01)
A61B 17/34 (2006.01)
(52) U.S. Cl.
CPC .... *A61N 1/0526* (2013.01); *A61B 2017/3411* (2013.01); *A61M 2205/054* (2013.01); *A61M 2210/0612* (2013.01)

(56) References Cited

FOREIGN PATENT DOCUMENTS

| WO | 00/07530 A2 | 2/2000 | |
|---|---|---|---|
| WO | 2006/052557 A2 | 5/2006 | |
| WO | 2006/123248 A2 | 11/2006 | |
| WO | 2007/052730 A1 | 5/2007 | |
| WO | 2009/122030 A1 | 10/2009 | |
| WO | 2013/024436 A1 | 2/2013 | |
| WO | WO-2016083669 A1 * | 6/2016 | ........... A61F 9/0026 |

OTHER PUBLICATIONS

Feb. 3, 2016 Extended Search Report issued in European Patent Application No. EP 15305548.8.
Oct. 26, 2016 Search Report issued in International Patent Application No. PCT/EP2016/058138.
Oct. 26, 2016 Written Opinion issued in International Patent Application No. PCT/EP2016/058138.

* cited by examiner

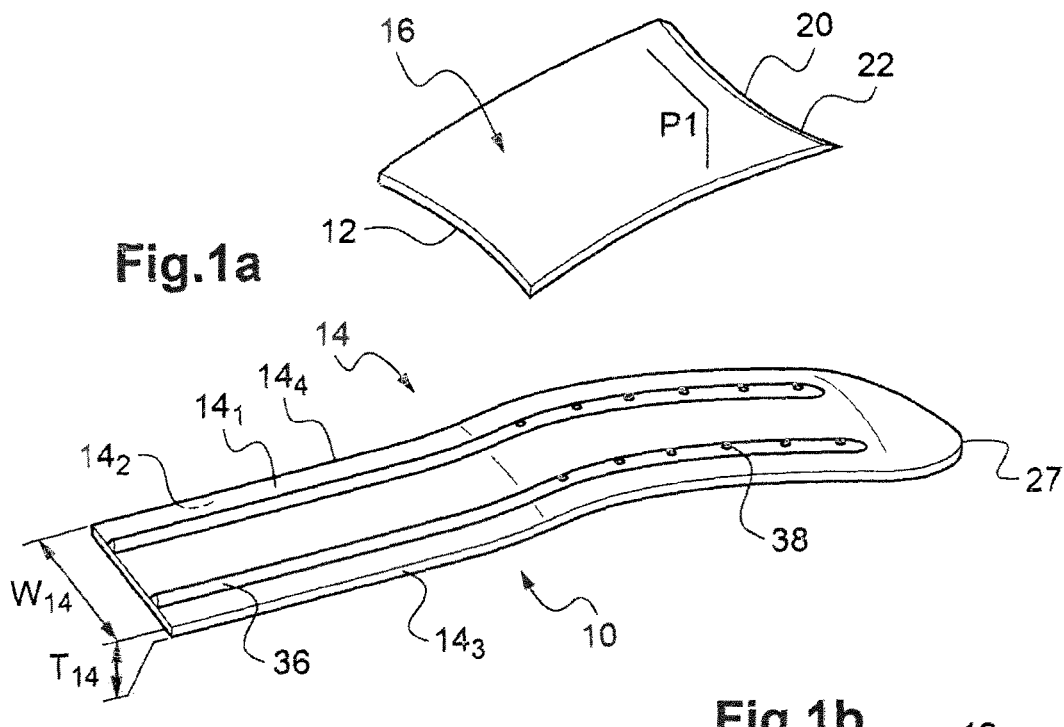
Fig.1a
Fig.1b
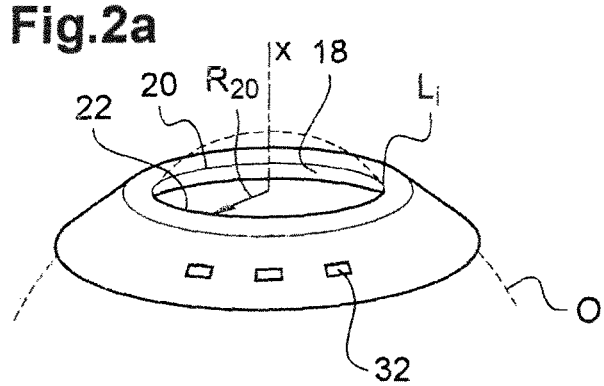
Fig.2a
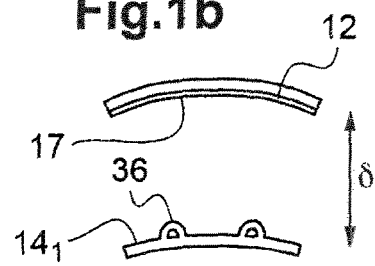
Fig.2b
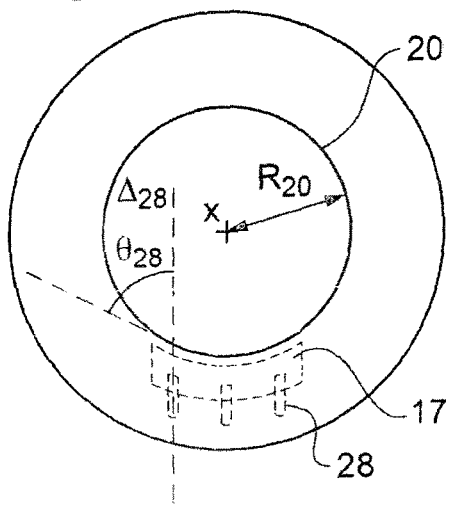
Fig.2c
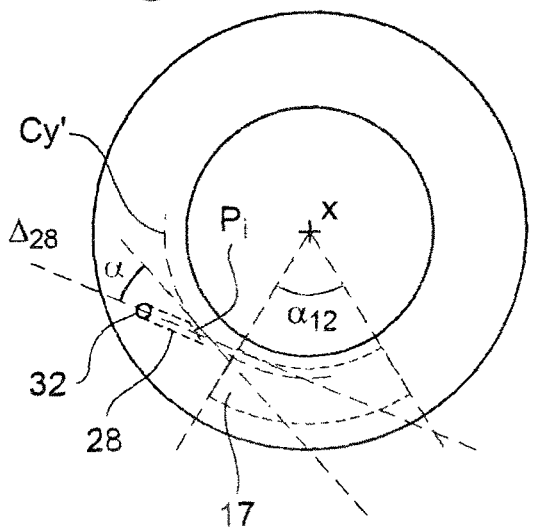

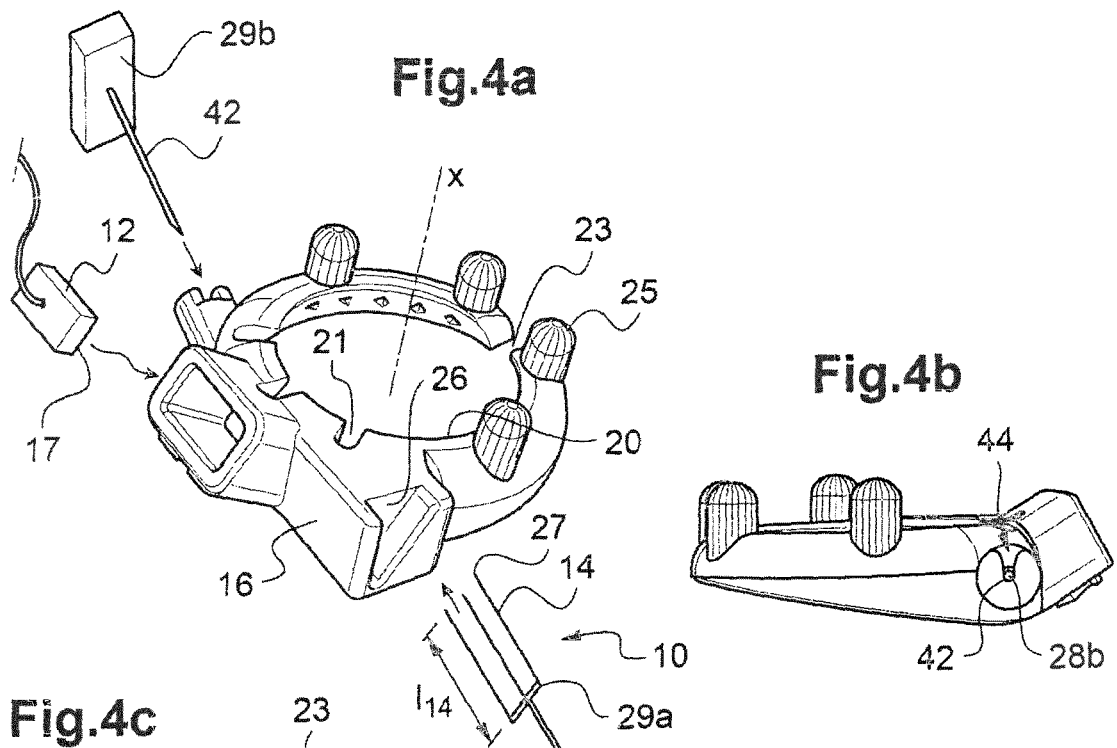
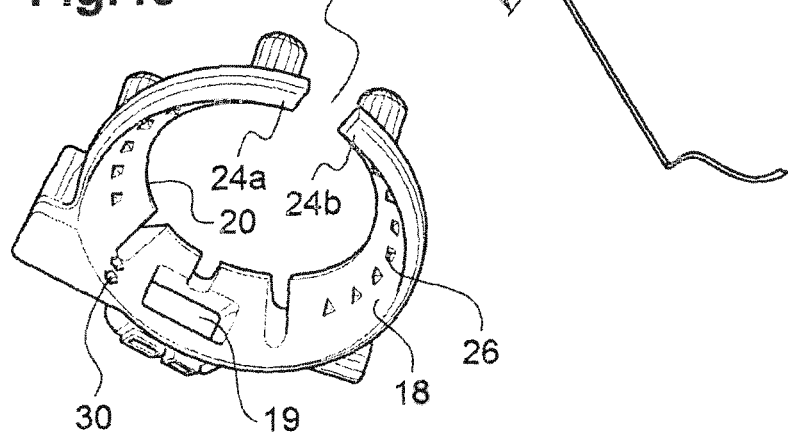
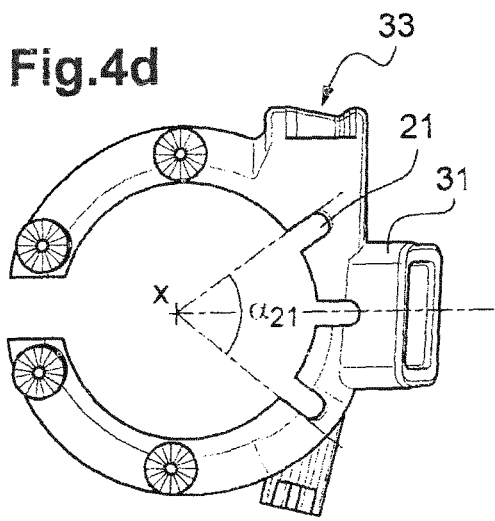
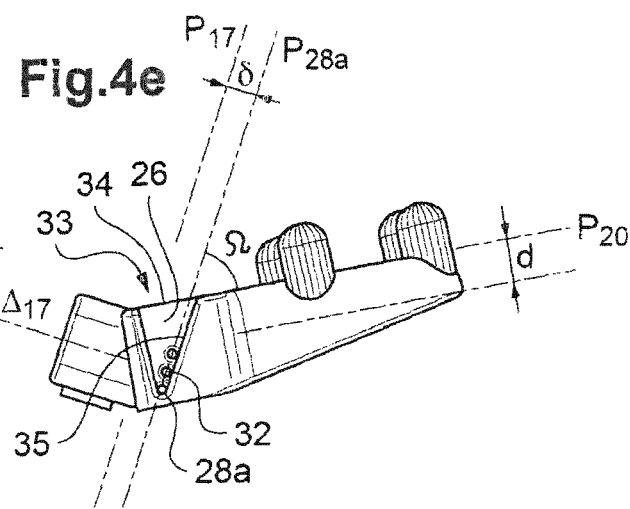

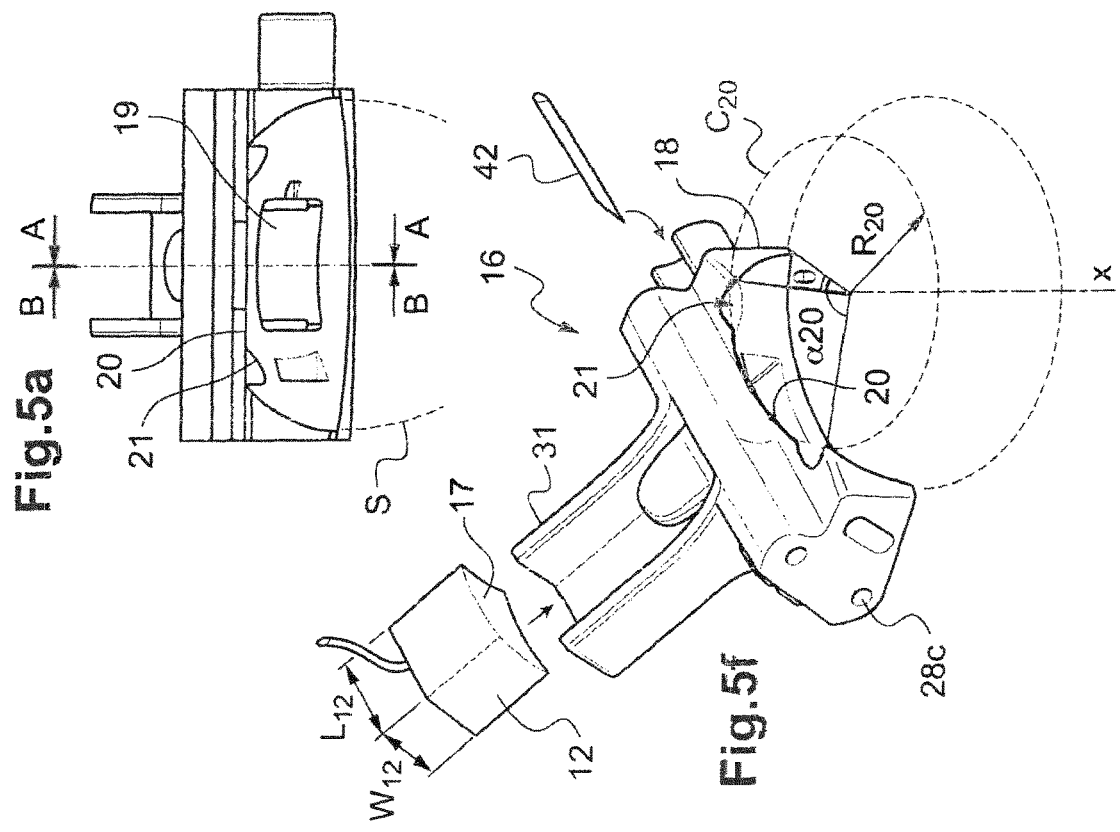
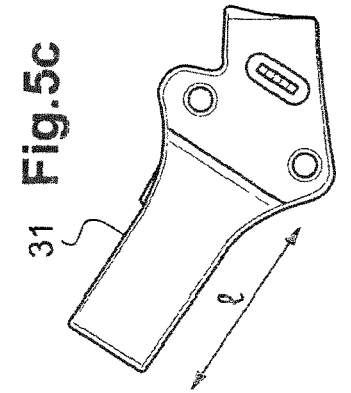
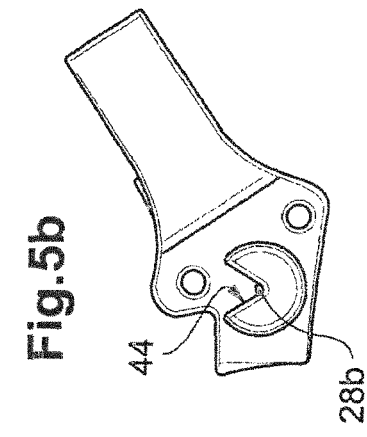
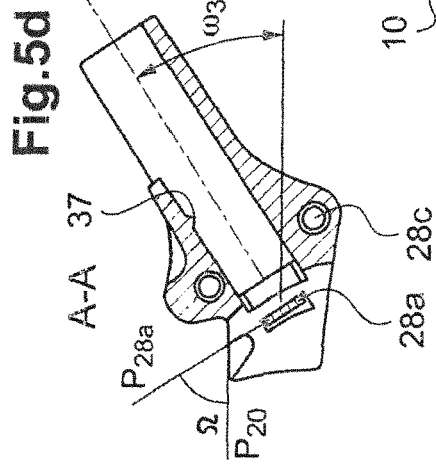
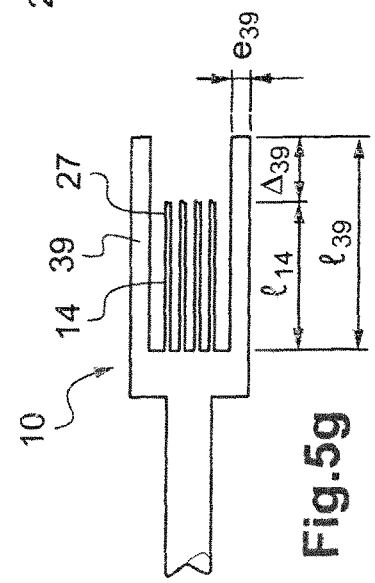
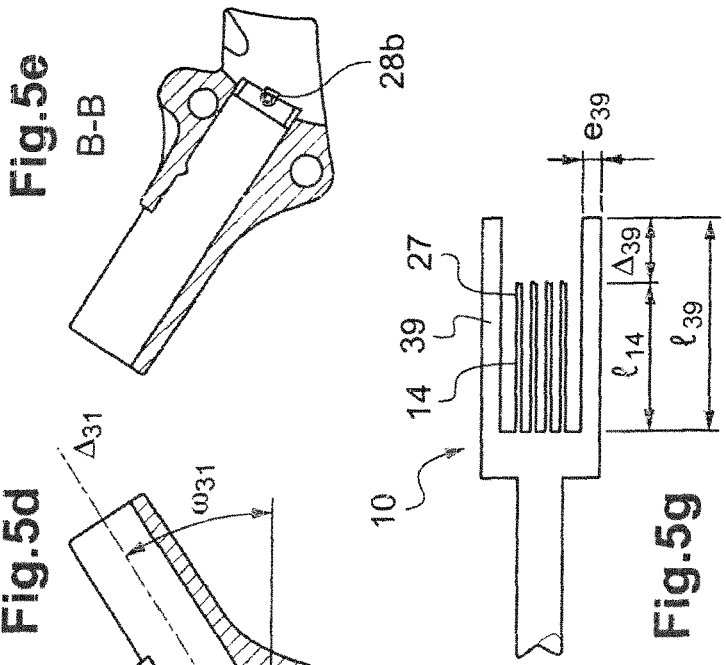

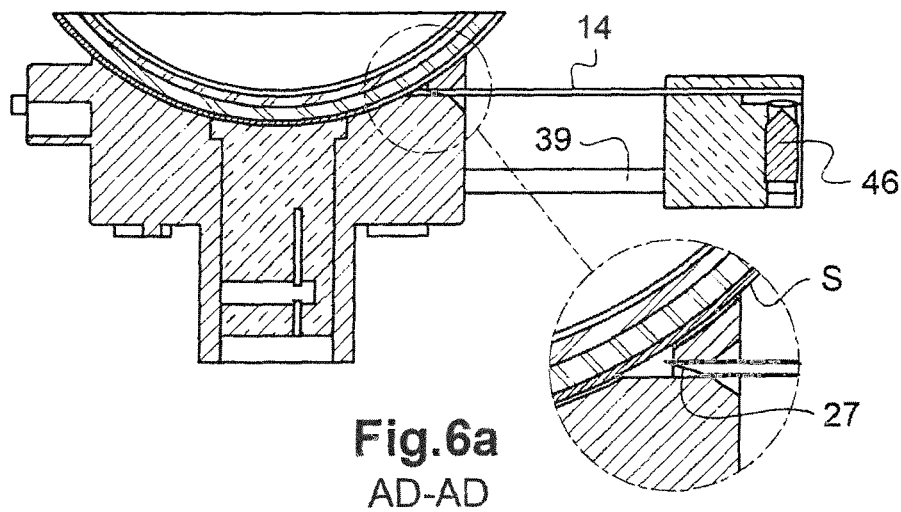
Fig.6a
AD-AD
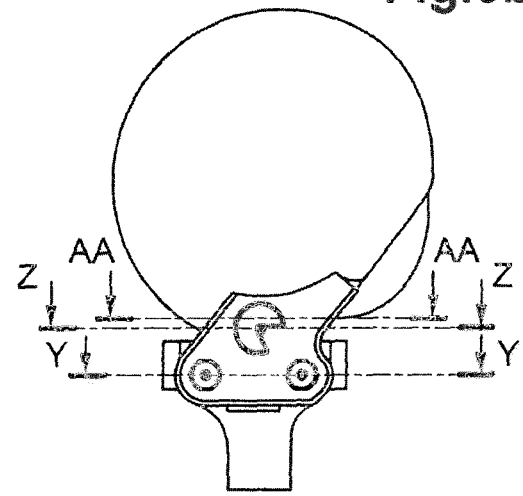
Fig.6b
Fig.6c
AC-AC
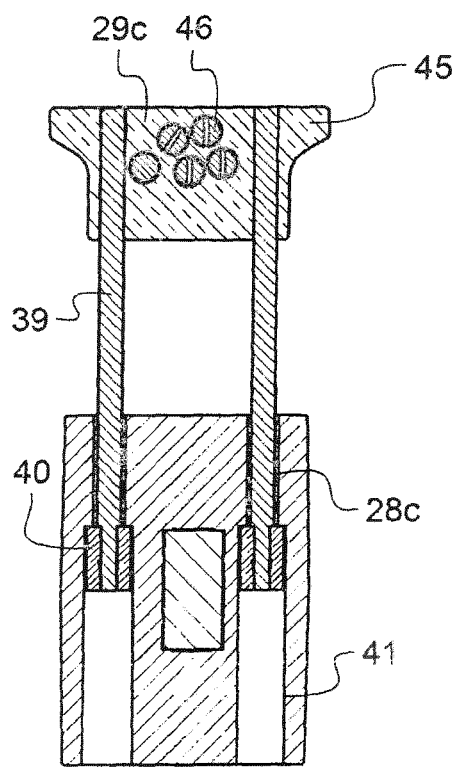
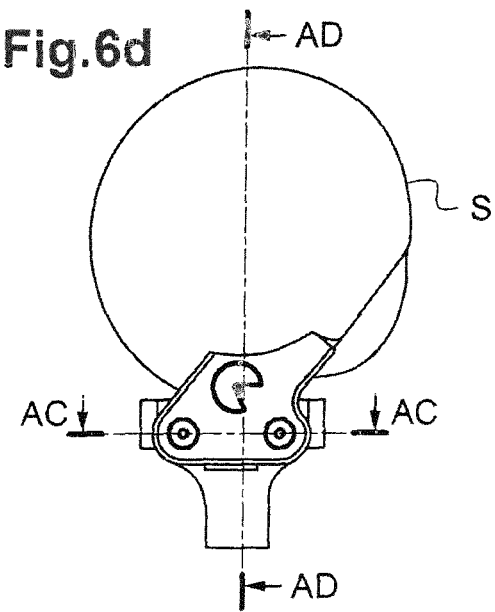
Fig.6d

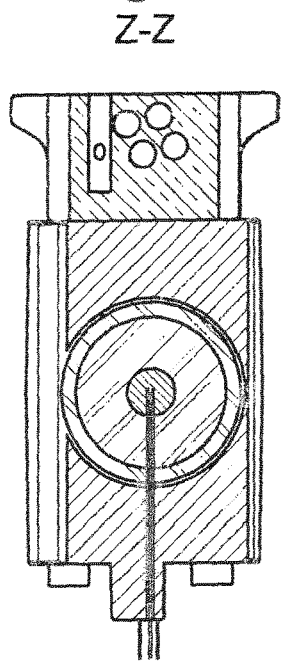
Fig.6f Z-Z
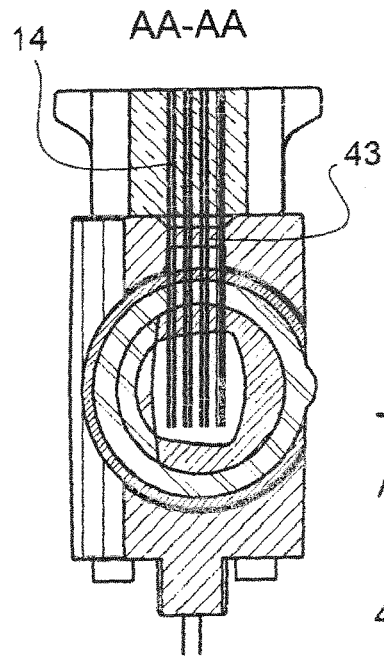
Fig.6g AA-AA
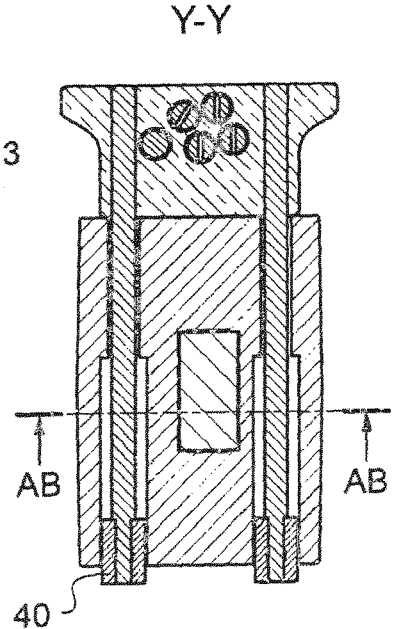
Fig.6h Y-Y
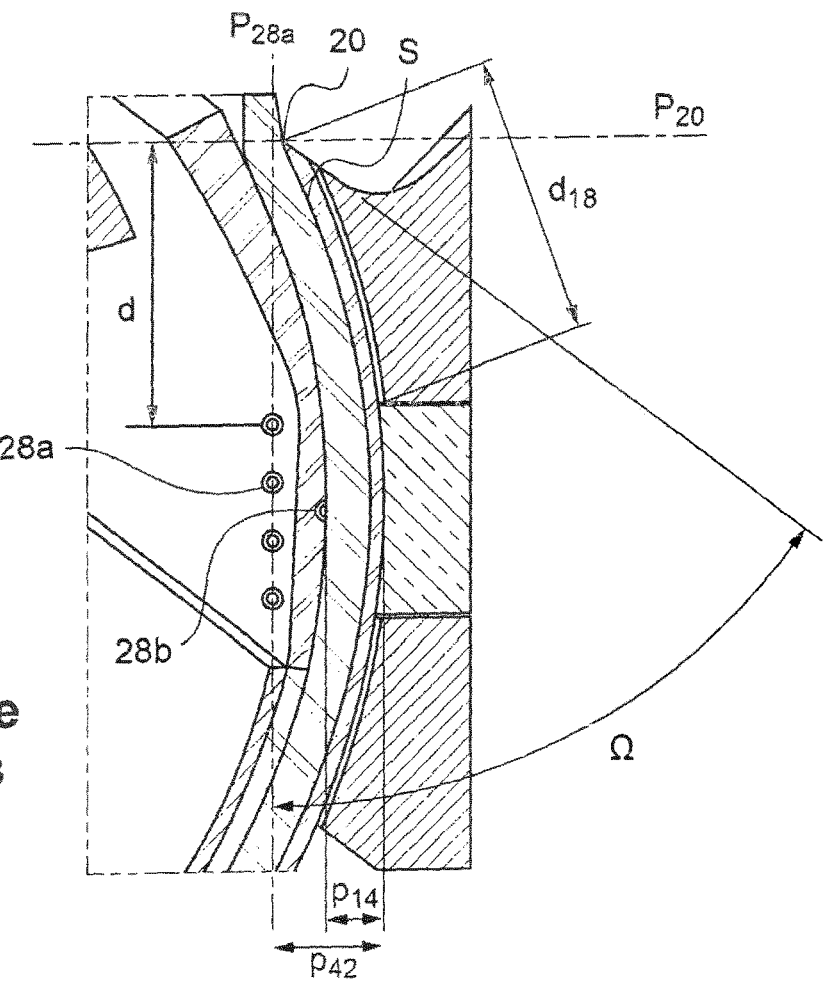
Fig.6e AB-AB

ELECTROPORATION DEVICE

TECHNICAL FIELD

The present invention relates to a device to electroporate a product into an eye, and in particular in the ciliary muscle.

PRIOR ART

WO 2006/123248 describes a device for administering a product by electroporation.

WO 00/07530, WO 2007/052730 and WO 2006/052557 describe injection devices.

It is an object of the invention to make available a new electroporation device which permits
a precise and stable positioning of the electrodes;
a limited risk of injury; and
the generation of an efficient large electrical field.

SUMMARY OF THE INVENTION

To this end, the invention proposes an electroporation device for injecting a product into an eye, and in particular into a ciliary muscle of an eye, said device comprising:
a support having a support contact surface extending along a virtual sphere having a radius between 10 and 15 mm, so as to match the outside surface of the eye,
a first electrode comprising an invasive electrode needle,
a second electrode having an electrically conductive electrode contact surface,
optionally an injection needle, According to a first main embodiment, the support comprises an insertion guide configured to guide a sliding of said electrode needle and/or injection needle along a respective insertion axis, so that the angle $\omega$ between said insertion axis and a plane $P_S$ tangential to the virtual sphere at the insertion point is less than 40°, preferably less than 35°, preferably less than 30°, preferably less than 28°, and/or greater than 10°, preferably greater than 15°, preferably greater than 20°, the insertion point being the point where said insertion axis crosses said virtual sphere.

The inventors have discovered that this configuration enables a very precise and efficient electroporation for a product injected into the ciliary muscle. In particular, it enables the electrode needle to extend in front of the electrode contact surface, substantially parallelly to the electrode contact surface.

Preferably, the angle $\omega$ for the insertion axis of an injection needle is less than 25°, preferably less than 23°.

Preferably, the angle $\omega$ for the insertion axis of at least one electrode needle is greater than 25°. In a preferred embodiment, the angle $\omega$ is substantially the same for all the electrode needles.

Preferably, the angle between said insertion axis and a plane tangential to the electrode contact surface, preferably at least a plane perpendicular to the main axis of the electrode contact surface, preferably any plane tangential to the electrode contact surface, preferably a general plane of the electrode contact surface is less than 20°, preferably less than 15°, preferably less than 10° or less than 5°. Therefore, the insertion axis is substantially parallel to the electrode contact surface.

Preferably, the support comprises at least two, or exactly three, four, five or more electrode insertion guides, preferably parallel to each other, which extend in a common plane which defines with a plane tangential to the electrode contact surface, preferably at least a plane perpendicular to the main axis of the electrode contact surface, preferably any plane tangential to the electrode contact surface, an angle less than 20°, preferably less than 15°, preferably less than 10° or less than 5°. The electrode needles can therefore define a net, preferably a grid, extending in front of and substantially parallelly to the electrode contact surface. Advantageously, the electroporation is homogeneous.

According to a second main embodiment, at least along a part of its length, the electrode needle is flattened and has
a width $W_{14}$ comprised between 0.2 and 2.0 mm, and
a thickness $T_{14}$ such that
the ratio $W_{14}/T_{14}$ being greater than 3.

According to a third main embodiment, the support comprises an insertion guide configured to guide a sliding of said electrode needle and/or injection needle along a respective insertion axis, and the support defines a circular rim, preferably an open circular rim, i.e. defining a part of a circle, having an axis X and a radius of greater than 5 mm and of less than 8 mm, so as to match the limbus of an eye, and the insertion axis defines, at the insertion point, an angle $\alpha$ less than 50°, preferably less than 45°, preferably less than 40°, with a plane $P_{Cy'}$ tangential to a cylindrical surface Cy' of axis X containing the insertion point and having a circular base.

Preferably, the angle $\alpha$ for the insertion axis of an injection needle is less than 35°, preferably less than 30°, preferably less than 28°, and/or greater than 10°, preferably greater than 20°, preferably greater than 25°.

Preferably, the angle $\alpha$ for the insertion axis of at least one electrode needle is less than 35°, preferably less than 33°, and/or greater than 10°, preferably greater than 20°, preferably greater than 25°, preferably greater than 30°.

Preferably, the angle $\alpha$ for the insertion axis of at least one electrode needle is less than 38°, and/or greater than 30°, preferably greater than 35°.

Preferably, the support comprises at least two electrode insertion guides, preferably parallel to each other, which extend in a common plane which defines with the plane of the rim an angle $\Omega$ which is greater than 40°, greater than 45°, preferably greater than 50°, and/or less than 80°, preferably less than 70°, preferably less than 60°, preferably less than 55°.

According to a fourth main embodiment, the first electrode and/or the injection needle comprises a guiding rod, extending parallel to the electrode needle(s) and/or to the injection needle, respectively, and the support comprises corresponding rod insertion guide(s).

Preferably, the insertion guide(s) is(are) holes which do not cross the virtual sphere on which the support contact surface extends.

Preferably, the guiding rod(s) of the first electrode and/or the injection needle extends beyond the tip of the electrode needle(s) of the first electrode and/or of the injection needle, respectively, by a distance which is preferably greater than 2 mm and less than 5 mm.

Preferably, the largest transversal dimension of a guiding rod is greater than 0.5 mm, preferably greater than 0.8 mm, preferably greater than 0.9 mm, and/or less than 2.0 mm, preferably less than 1.5 mm, preferably less than 1.2 mm.

Preferably, the device comprises a needle stop that is able to limit the axial movement of the guiding rod. Preferably, the needle stop makes impossible the complete extraction of the guiding rod out of the corresponding insertion guide, i.e. hinders any dismounting of the guiding rod from the support.

The inventors have discovered that the features of these main embodiments are advantageous for the efficiency of the electroporation.

The characteristics of the different main embodiments of the invention, optional or not, as well as the optional characteristics in the following description may be combined or not. For instance, in the first main embodiment, the first electrode may be a flattened electrode or not.

Preferably, whatever the main embodiment, the device comprises one or several of the following optional and preferred characteristics:

- The insertion axis of the electrode needle defines an angle with a plane perpendicular to the main axis of the electrode contact surface, said angle being less than 20°, preferably less than 10°, preferably less than 5°;
- Preferably, all the electrode insertion guides extend parallel to each other in a common plane;
- The first electrode comprises a plurality of parallel invasive electrode needles extending in a common plane, the angle between said plane and the general plane in which the second electrode extends being less than 10°;
- The support defines a circular rim, preferably an open circular rim, having an axis X and a radius of greater than 5 mm and of less than 8 mm, so as to match the limbus of an eye, said rim being interrupted by at least one notch, preferably located in a portion of the rim which extends along an angular sector less than 120° and centred on a median plane of the second electrode;
- In a close position, the portion of said electrode needle which extends in front of the electrode contact surface is greater than 1 mm, preferably greater than 2 mm, preferably greater than 3 mm, preferably greater than 5 mm, preferably greater than 6 mm.
- The length of said electrode needle is determined so that, in a front view of the second electrode, the inserted electrode needle faces the electrode contact surface and extends, in a close position, so as to completely cross, i.e. "bar", the electrode contact surface defined by the second electrode;
- The surface area of the electrode contact surface is greater than 6 mm$^2$ and less than 20 mm$^2$;
- The electrode contact surface preferably defines a spherical contact surface which preferably extends on the same virtual sphere as the support contact surface;
- Preferably, the complete contact surface defined by the support contact surface and the electrode contact surface has the shape of an open circular band;
- The support presents the general shape of an open ring, so that it presents a gap between a first end and a second end, and, preferably,
  - the support is made in a material which exhibits a plastic behaviour, so that the support may be manually plastically deformed to modify the distance between said first and second ends, and/or
  - said gap is preferably disposed substantially opposite to the second electrode, and/or
  - the support preferably comprises two holding posts positioned at said ends of the support;
- The support comprises prepositioning guide(s) configured to guide said electrode needle and/or said injection needle into a position wherein said electrode needle and/or said injection needle is(are) in line with an insertion axis of a corresponding insertion guide;
- The support contact surface and/or the electrode contact surface are defined by a material which is biocompatible, and in particular, which is can be put in contact with surface of the eye without prejudice;
- The support contact surface and/or the electrode contact surface are defined by a material which is a polycarbonate, for instance sold by Bayer;
- The electrode contact surface is defined by brass;
- The device comprises
  - an injection needle, and
  - electrode insertion guide and injection needle insertion guide configured to guide a sliding of said electrode needle and injection needle along respective electrode needle insertion axis and injection needle insertion axis, any plane perpendicular to said electrode needle insertion axis being parallel to any plane perpendicular to said injection needle insertion axis, and, preferably parallel to the main axis of the electrode contact surface;
- In a close position of the injection needle, the maximal depth of the injection needle under the virtual sphere is between 0.8 mm and 1.0 mm, and/or, in a close position of the electrode needle, preferably of any electrode needle, the maximal depth of the electrode needle under the virtual sphere is between 1.5 mm and 1.8 mm;
- The device comprises a reservoir containing said product and an injection needle in fluid communication with said reservoir, said product being a therapeutic nucleic acid of interest, preferably a desoxyribonucleic acid molecule or a ribonucleic acid molecule.

The invention also concerns an electroporation method for injecting a product into an eye, in particular in the ciliary muscle of an eye, by means of a device according to the invention, said method comprising the following steps:

a) placing the electrode contact surface on the outside surface of said eye, preferably so that a rim of the support bears on the limbus of said eye (edge of the cornea),
b) inserting the electrode needle(s) of the first electrode into corresponding insertion guide(s) of the support preferably so that the ciliary muscle extends, at least partially, between the electrode needle(s) of the first electrode and the second electrode,
c) before or after step b), preferably after step b), inserting an injection needle into the eye, preferably while being guided by a corresponding insertion guide, so that its tip preferably reaches the ciliary muscle of said eye,
d) injecting said product into the eye,
e) generating an electrical field between the electrode needle(s) of the first electrode and the second electrode, the electrical field being adapted to promote electroporation.

Definitions

When a needle is mobile and guided by the support, its position corresponding to its full insertion is called the "close position". In the present description, unless otherwise stated, any position of the first electrode is referring to the close position and any position of the second electrode is referring to the position of the second electrode when it is attached to the support and ready for service.

The "service position" corresponds to the configuration adapted for electroporation of the product, in particular in the ciliary muscle: The electrode contact surface and the support contact surface bear on the eye, with the first electrode in its close position.

A "flattened" needle does not mean that the needle is necessarily flat, i.e. extends in a plane. It means that the needle has a thickness which is much smaller that its width, preferably at least 5 times smaller.

The "insertion point" of a needle is the point where, in the close position, said needle crosses the virtual sphere bearing the support contact surface. When this needle is guided, the insertion point corresponds to the point where the insertion axis crosses the virtual sphere. Preferably, the insertion points correspond to an outlet orifice of an insertion guide.

A "spherical contact surface" means a substantially spherical contact surface, preferably so as to correspond to the shape of the anterior or posterior part of the outside surface of an eye.

The "main axis" of a surface is the direction perpendicular to said surface passing through its centre.

A "quadrant of a hemisphere" designates a quarter of the surface of this hemisphere obtained by cuts in two perpendicular planes that intersect along the main axis of the hemisphere.

"First" and "second", or "upper" and "lower", or "right-hand" and "left-hand" are used to distinguish corresponding elements, but do not limitate the invention.

In the present description, unless otherwise stated, "comprising a" should be understood as "comprising at least one".

BRIEF DESCRIPTION OF THE FIGURES

Other features and advantages of the invention will become clear upon reading the non limitative following detailed description and by examining the non limitative attached drawing, in which:

FIGS. 1a and 1b show, in perspective and along the transverse plane P1, a first embodiment of a device according to the invention;

FIG. 2a shows, in perspective, a second embodiment of a device according to the invention;

FIGS. 2b and 2c show, view from above, along the axis X, the second embodiment of FIG. 2a and a variation of this second embodiment, respectively;

FIGS. 4a-4e show, in different views, a fourth embodiment of a device according to the invention, FIGS. 5a-5f represent the most preferred embodiment of the invention, in a front view, in a right view, in a left view, in cross-section AA, in cross-section BB and in perspective, respectively, FIG. 5g represents a preferred embodiment of the first electrode, FIGS. 6a-6h represent another most preferred embodiment of the invention, in a right view for FIGS. 6b and 6d, and in different cross-sections in the other figures.

Figure 3A:
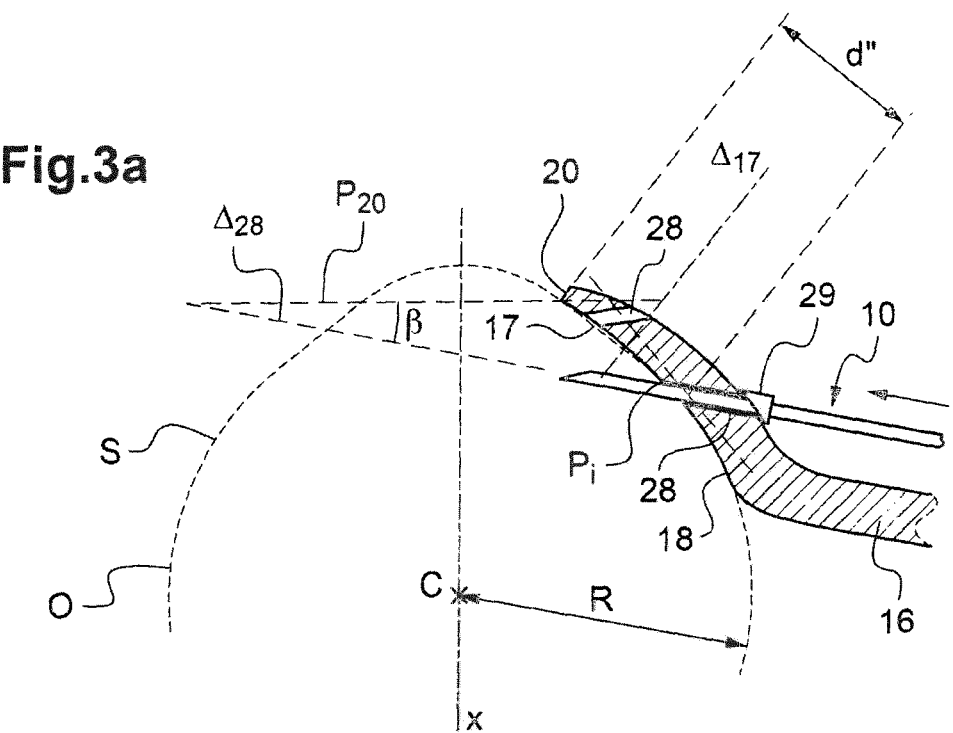
FIGS. 3a and 3a' show, in a cross section, a third embodiment of a device according to the invention.

In the embodiment of FIG. 3a, the side view of the electrode needle is observed perpendicularly to the plane in which, in the close position, the inserted part of the electrode needle substantially extends and which is perpendicular to the rim 20.

In the various figures, identical reference signs are used to designate identical or similar elements.

DETAILED DESCRIPTION

The figures represent examples of devices according to the invention.

Each of these devices comprises a first electrode 10, a second electrode 12, and a support 16. The second electrode defines an electrode contact surface 17 designed to contact the surface of the eye.

Support

The support defines a spherical support contact surface 18. This support contact surface extends along a virtual sphere S corresponding to the outside surface of an eye O so that, in the service position, it can bear on the outside surface of said eye.

Preferably, the support 16 also defines a circular rim 20, having an axis X, which partially defines the limit of the support contact surface 18.

General Shape

Preferably, the support has the general shape of a ring around the axis X, as represented in FIG. 2a, or of a part of a ring as represented in FIG. 4 or in FIG. 5.

In FIG. 4, the support 16 has a general shape of a ring which is interrupted by a gap 23 separating a first end 24a and a second end 24b. Said gap is preferably greater than 0.5 mm, preferably greater than 1 mm, and/or less than 8 mm, less than 6 mm, less than 5 mm, less than 4 mm.

Preferably, when the ring is interrupted, as in the embodiment of FIG. 4, the support is made in a material which exhibits a plastic behaviour, so that the support may be manually plastically deformed to modify the distance between said first and second ends. Advantageously, the support 16 may be deformed to different sizes of eyes.

The gap is preferably disposed substantially opposite to the second electrode, which makes the manipulation of the support easier.

Preferably, the ring extends laterally over an angle sector $\alpha_{20}$ of greater than 45°, preferably greater than 60°, preferably greater than 80°, preferably greater than 100°, preferably greater than 120°, preferably greater than 130°, preferably greater than 135°, and/or less than 180°, preferably less than 170°, preferably less than 160°, preferably less than 150°, preferably less than 140° (see FIG. 5f).

The support preferably comprises a holding post, preferably at least two holding posts 25, preferably four holding posts 25, preferably positioned at the first and second ends of the support, respectively. The holding posts make the manipulation of the support easier. The holding posts 25 are on the upper surface of the support, preferably on a portion of the outside surface which is opposite to the support contact surface 18, and are preferably at least partly located on the part of the support which is opposite to the second electrode.

The support contact surface 18 preferably bears one, preferably several spikes 26 which are protruding from said surface and designed so as to limit the sliding of the support on the eye. The support preferably comprises more than 2, more than 5, more than 10, more than 20 spikes 26. The height of said spikes is preferably more than 0.1 mm and/or less than 0.5 mm or less than 0.3 mm.

In one embodiment, the support is designed to be able to keep the eyelids open during the stage of penetration of the electrode needle.

The support may also bear elastic means, for instance a spring, configured to force the first electrode and/or an injection needle toward the close position and/or to push the second electrode on the surface of the eye.

The support 16 is preferably in a polymeric material. It is preferably in a material which is not electrically conductive.

The support is preferably made of a transparent material for a better observation by the user.

The support can be used for manipulation of the device. As represented in FIG. 5, the support can in particular comprise a handle 31 allowing the injection device to be gripped, for example, between a thumb and an index finger of one hand. Manipulation of the device is made much easier in this way.

Preferably, the handle extends along an axis $\Delta_{31}$ which is inclined, relatively to the plane of the rim, with an angle $\omega_{31}$ greater than 25°, preferably greater than 30° and/or less than 45°, less than 40°, less than 35°.

When the first electrode 10 comprises several coplanar electrode needles guided by corresponding coplanar electrode insertion guides, the handle preferably extends substantially along an axis $\Delta_{31}$ substantially perpendicular to the plane containing said electrode insertion guides.

The length $l_{31}$ of the handle 31 is preferably greater than 5 mm or 8 mm and preferably less than 50 mm, 30 mm, 20 mm, 15 mm.

Support Contact Surface

The width of the support contact surface 18 may be constant or not. In the embodiment of FIG. 4, the width of the support contact surface is larger in the neighbourhood of the second electrode than in the neighbourhood of the two ends 24. Advantageously, the risk of injury is limited.

The radius of curvature R of the support contact surface 18 preferably ranges between 10 mm and 15 mm, preferably between 11 mm and 14 mm, preferably between 12 mm and 13 mm, and is preferably about 12.5 mm. The stability of the support on the eye is therefore greatly improved.

In one embodiment, the support contact surface 18 has a surface area of greater than 50 mm$^2$, preferably of greater than 100 mm$^2$, preferably of greater than 120 mm$^2$, preferably of greater than 140 mm$^2$, preferably of greater than 150 mm$^2$, preferably of greater than 160 mm$^2$, and/or of less than 200 mm$^2$, preferably of less than 180 mm$^2$.

The support contact surface 18 may be solid or can be locally interrupted by holes.

In a preferred embodiment, the support contact surface 18 is interrupted by a hole 19 for the introduction of the second electrode (see FIGS. 4 and 5).

Preferably, the support contact surface 18 does not extend over more than one quadrant of a hemisphere.

In a preferred embodiment, the support contact surface 18 has the general shape of a circular band, preferably an open circular band.

Seen from the front, the support contact surface 18 can have a substantially parallellepipedal contour, for example a rectangular contour, or a substantially trapezoidal contour.

The support contact surface 18 can have two large sides and two small sides. The large sides can in particular form rounded corners with the small sides.

The length of the small sides can be greater than 3 mm, preferably greater than 4 mm, and/or less than 10 mm, preferably less than 8 mm, preferably less than 7 mm, preferably less than 6 mm. The length of the large sides can be greater than 10 mm, preferably greater than 12 mm, preferably greater than 14 mm and/or less than 20 mm, preferably less than 18 mm, preferably less than 16 mm.

Preferably, the support is configured so that, when the support contact surface 18 bears on the surface of the eye, the support can only contact the surface of the eye by way of the support contact surface 18.

Rim

The rim 20 has the shape of an arc of a circle $C_{20}$ (including a complete circle) having an axis X and a radius $R_{20}$ of greater than 5 mm, preferably of greater than 5.5 mm, preferably of greater than 5.8 mm, and of less than 8.0 mm, preferably of less than 7.0 mm, preferably of less than 7.5 mm, preferably of less than 6.0 mm. Such a rim has a shape substantially corresponding to the limbus $L_i$ of the eye. It may be placed in contact with this limbus, so as to encircle at least partially, possibly completely, said limbus.

The stability of the support is greatly improved when the rim 20 is designed to bear on the limbus of the eye.

Preferably, the second electrode does not define, even partly, any such rim. In a preferred embodiment, only the support defines a rim configured to bear on the limbus.

The rim 20 may have the shape of a complete circle, as in FIG. 2a. Advantageously, in the service position, the stability of the device is increased. However, preferably, the rim 20 is open, i.e. is not closed on itself, as represented in FIG. 4. Preferably, the rim 20 is largely opened, as represented in FIG. 5, which makes its handling easier.

The length of said arc of a circle is preferably greater than 5 mm, preferably greater than 10 mm, preferably greater than 12 mm, preferably greater than 13 mm, greater than 14 mm, and/or preferably less than 45 mm, preferably less than 40 mm, less than 35 mm, preferably less than 30 mm, preferably less than 25 mm, preferably less than 20 mm, preferably less than 17 mm, preferably less than 15 mm.

The support is preferably provided with a flexible skirt 22 extending along said rim (see FIG. 2a), the flexible skirt being preferably made of a material chosen in the group formed of polymers of silicone, conductive sponge, in particular synthetic sponge, polyester, polyorthoester, polymethyl methacrylate or of any other flexible medical-grade polymers.

Preferably, the rim is interrupted by at least one notch 21, preferably at least two notches, preferably three notches. The notches 21 are configured so that the physician may see the limbus of the eye through them when positioning the support onto the eye. At least one notch, preferably all the notches are located in the neighbourhood of the second electrode.

In FIGS. 4 and 5, the support comprises two and three notches 21, respectively, which interrupt the rim 20 in the neighbourhood of the second electrode. Indeed, it is in this region that the positioning of the support is of utter importance.

Preferably, the notch(es) (is) are located in a portion of the rim which extends along an angular sector $\alpha_{21}$ less than 120°, preferably less than 100°, said angular sector being preferably centered on a median plane M of the second electrode (see FIG. 4d).

The positioning of the device on the eye is advantageously made simpler and more precise.

Electrodes

By definition, the first and second electrodes are designed to be electrically connected to first and second terminals, respectively, of an electrical generator.

The first and second electrodes comprise non represented first and second connectors for the electrical connection to said first and second terminals, respectively. The electrical generator is adapted to polarize differently said first and second electrodes so as to generate an electrical field enabling electroporation.

A device according to the invention may also include such an electrical generator.

First Electrode

The first electrode 10 may comprise one or several, preferably three, four or five, preferably parallel, preferably coplanar, preferably rectilinear electrode needles 14. The electrode needles are preferably fixed to each other so as to form a fork or a comb, as represented in FIG. 4a or FIG. 5g. The distance between the axis of two adjacent electrode needles is preferably greater than 0.5 mm, preferably greater than 0.6 mm, preferably greater than 0.7 mm, preferably greater than 0.8 mm, and/or less than 5 mm, preferably less than 3 mm, preferably less than 1.5 mm, preferably less than 1.2 mm, preferably less than 1.0 mm, preferably less than 0.9 mm.

Preferably, all the electrode needles have the same structure. In the following description, only one electrode needle 14 is described, but one or several of its features may be applied to any electrode needle of a first electrode comprising a plurality of electrode needles. In a preferred embodiment, all the electrode needles have the same structure.

Preferably, the length $l_{14}$ of an electrode needle 14 is greater than 8 mm, preferably greater than 10 mm, preferably greater than 11 mm, and/or less than 15 mm, preferably less than 14 mm, preferably less than 13 mm (see FIGS. 3a' and 4a).

Preferably, the insertion length $l_{14i}$ of an electrode needle, preferably of any electrode needle, i.e. which extends inside the virtual sphere S in the close position, is greater than 5 mm, preferably greater than 7 mm, preferably greater than 8 mm, and/or less than 13 mm, preferably less than 12 mm, preferably less than 11 mm (see FIG. 3a').

Preferably, the diameter of an electrode needle 14 is less than 0.5 mm, preferably less than 0.4 mm, preferably less than 0.35 mm. This characteristic is particularly advantageous when the electrode needle is inserted into the eye substantially tangentially to the surface of the eye, as in the embodiment of FIG. 4 or FIG. 5.

Preferably, the diameter of an electrode needle 14 is greater than 0.2 mm, preferably greater than 0.3 mm. Advantageously, the electrode needle is thereby stiff enough to be inserted in the eye, and in particular substantially tangentially to the surface of the eye.

For the same reason, the tip 27 of the electrode needle 14 is preferably bevelled for facilitating the penetration of the electrode needle into the eye, as represented in FIGS. 1a and 3a.

In an embodiment, any electrode needle 14 comprises an insulated part 14a which outside surface is electrically insulated, and a non insulated part 14b, preferably extending from the insulated part to the tip 27 of the electrode needle.

The insulated part 14a may be insulated, for example, by means of an insulating cover, preferably so that the electrically insulated part of said electrode needle may penetrate of at least 0.4 mm, at least 0.6 mm or at least 0.8 mm into the virtual sphere S in the close position.

As illustrated in FIG. 1, the electrode needle 14 may comprise a flattened part, i.e. is such that the ratio of its width and its thickness $W_{14}/T_{14}$ is greater than 3, preferably greater than 5, greater than 7, greater than 10, greater than 15, greater than 20, and/or less than 30 or less than 25. Preferably, the width $W_{14}$ is comprised between 0.15 and 2.0 mm, preferably greater than 0.20 mm, and/or the thickness $T_{14}$ is comprised between 0.15 and 0.5 mm, preferably greater than 0.20 mm.

The flattened part preferably represents more than 50%, more than 60%, more than 70%, more than 80% or more than 90% of the length of the insertion part which is to be inserted in the eye, i.e. which may protrude inside the virtual sphere S bearing the support contact surface 18.

Preferably, the flattened part extends up to the tip 27 of the insertion needle and/or along all the length of the electrically conductive part 14a, and even along all the length of the insertion part, and preferably all along the length of the electrode needle.

The flattened part preferably comprises upper and lower large faces $14_1$ and $14_2$, and right-hand and left-hand lateral faces $14_3$ and $14_4$, defining the thickness of the flattened part, i.e. the maximal distance between the two large faces.

The flattened part may be curved along its length (see FIG. 1a), and/or along its width (see FIG. 1b).

The flattened part 14 may have the shape of a chute or of a part of a sphere.

In a preferred embodiment, the upper large face $14_1$ at least partially extends substantially parallel to the contact surface of the second electrode.

In particular, at least in the region facing the electrode contract surface, the upper large face $14_1$ may have the shape of a sphere having the same centre as the virtual sphere S. Advantageously, the homogeneity of the electrical field between the first and second electrodes is improved if the electrode contact surface extends along said virtual sphere. The upper large face $14_1$ may also have a length and/or a width corresponding to that of the second electrode.

The flattened part 14 may have constant or variable length and/or width and/or thickness. In particular, it may be bevelled when the electrode needle is observed laterally, and/or from above, i.e. as observed perpendicularly to the large faces.

Preferably, in the active region of the upper large face, i.e. the region facing the second electrode in the close position, the thickness and/or the width of the flattened part is substantially constant.

Second Electrode

In FIGS. 2b and 2c, the second electrode is represented with a dashed line.

The electrode contact surface 17 preferably extends along the same virtual sphere S as the spherical support contact surface 18 of the support. It matches the outside surface of an eye O so that, in the service position, it can bear on the outside surface of said eye O.

Figure 3A:
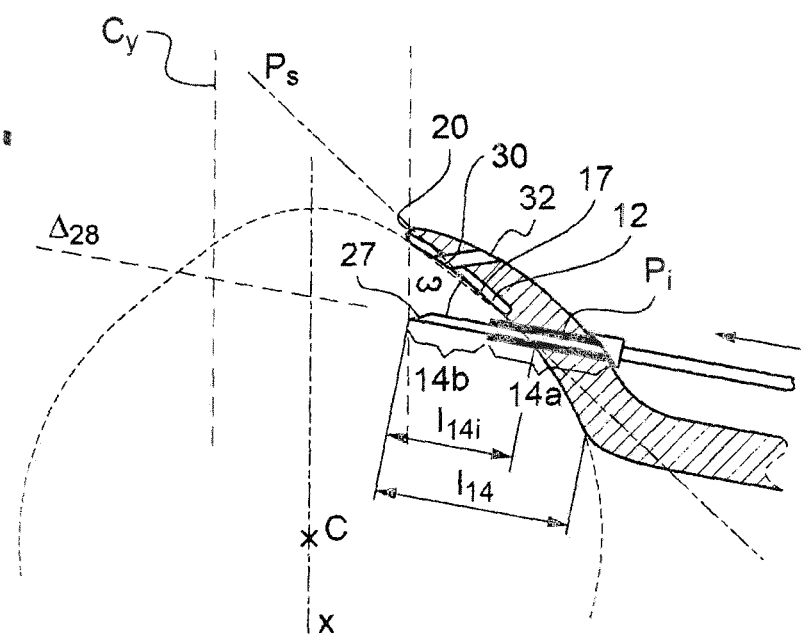

It may be an electrically conductive layer covering at least part of, preferably the whole surface of the support contact surface 18, as in the embodiments of FIGS. 2 and 3.

In the embodiments of FIGS. 4 and 5, the second electrode is not integral with the support, i.e. is a part which is initially independent of the support, then mounted onto the support.

Preferably, as represented in FIG. 4a, the second electrode can be removed, i.e. detached, from the support.

When the second electrode is to be mounted on the support (FIGS. 4 and 5), the support, in particular an handle of the support, is preferably configured to guide this mounting. In particular, the support may define a tube (FIG. 4) or of a gutter (FIG. 5), in which the second electrode may slide until an assembled position. Preferably, the support comprises an elastic tongue 37 or claw configured to fix the second electrode on the support in an assembled position, possibly in a reversible manner (see FIG. 5d).

The second electrode 12 is preferably a plate contact electrode made of an electrically conductive material.

The second electrode may also comprise a set of spikes, preferably extending perpendicularly to its contact surface 17. These spikes may be similar to the spikes 26 of the support. Preferably, the second electrode does not comprise any spike. Preferably, it is smooth.

The second electrode may define the circular rim 20. However, as represented in FIG. 4, the rim 20 is preferably defined by the support.

The electrode contact surface 17 is preferably substantially surrounded by the support contact surface 18.

Preferably, the distance $d_{18}$ between the rim 20 and any point of the electrode contact surface 18 is greater than 2 mm, preferably greater than 2.5 mm, preferably greater than 3 mm, preferably greater than 3.5 mm, preferably greater than 4.0 mm, and/or less than 6 mm, preferably less than 5 mm, preferably less than 4.5 mm (see FIG. 6e).

Preferably, the electrode contact surface does not extend over more than one quadrant of a hemisphere.

Preferably, the second electrode extends within an angular sector $\alpha_{12}$ around the axis X (see FIG. 2c) which is less than 90°, preferably less than 60°, preferably less than 50°, preferably less than 45°, preferably less than 35°, preferably less than 30°, and/or preferably greater than 10°, preferably greater than 15°, preferably greater than 20°.

The surface area of the electrode contact surface is preferably greater than 3 mm$^2$, greater than 4 mm$^2$, greater than 5 mm$^2$, greater than 6 mm$^2$, greater than 8 mm$^2$, greater than 10 mm$^2$, greater than 11 mm$^2$, greater than 12 mm$^2$, greater than 15 mm$^2$, greater than 17 mm$^2$, and/or less than 90 mm$^2$, less than 60 mm$^2$, less than 30 mm$^2$, less than 20 mm$^2$.

In a front view, the electrode contact surface has preferably a substantially rectangular shape. In said front view, the length $l_{12}$ of the second electrode is preferably greater than 3 mm, greater than 4 mm, greater than 5 mm, and/or less than 8 mm, less than 7 mm. In said front view, the width $w_{12}$ of the second electrode is preferably greater than 1 mm, preferably greater than 2 mm, and/or less than 4 mm.

Injection Needle

Preferably, the device comprises an injection needle 42.

The injection needle may be part of the first electrode and/or of the second electrode and/or of the support. In particular, it may be in an electrically conductive material so as to constitute or be a part of the first and/or second electrodes. In particular, an electrode needle 14 of the first electrode may be an injection needle.

On the contrary, and preferably, the injection needle may be independent of the first and second electrodes, as in FIG. 4 or 5.

Preferably, the injection needle is configured so that it can only penetrate into an eye so that the maximal depth $p_{42}$ of the injection needle under the outside surface of the eye is comprised between 0.6 mm and 1.3 mm, preferably greater than 0.7 mm, preferably greater than 0.8 mm, preferably greater than 0.85 mm, and/or less than 1.2 mm, preferably less than 1.1 mm, preferably less than 1.0 mm, preferably less than 0.95 mm.

The injection needle may in particular have one or several characteristics of the injection needle disclosed in WO 2009/122030, or U.S. Ser. No. 12/921,979, incorporated by reference.

Preferably, the insertion length of the injection needle is greater than 2 mm, preferably greater than 3 mm, preferably greater than 3.5 mm, preferably greater than 4.0 mm, and/or less than 7.0 mm, preferably less than 6.0 mm, preferably less than 5.5 mm.

Preferably, the ratio of the insertion length of the injection needle on the maximal insertion length of any electrode needle is between 0.3 and 0.7, preferably between 0.4 and 0.6, preferably about 0.5.

Preferably, the insertion length of the injection needle and the position of a corresponding injection needle insertion guide are determined so that, in the close position of the injection needle and of a plurality of electrode needles, the tip of the injection needle is at the centre of a grid defined by the electrode needles inside the virtual sphere S, when observed along the main axis $\Delta_{17}$ of the electrode contact surface 17 (see FIG. 6g).

The injection needle may comprise an injection channel 36, having one or more ejection orifices 38.

One or several, or all the ejection orifices 38 may open out axially relative to the main axis of the injection needle, as represented in FIG. 3a, or not. In particular, one or several, or all the ejection orifices 38 may open out on a large face (as represented in FIG. 1a) and/or on a lateral face of a flattened part of an electrode needle.

The ejection orifices are preferably homogeneously spread on a large face of the flattened part.

As represented in FIG. 1a, an injection channel 36 may be fixed on the electrode needle 14, and in particular on a large face of a flattened electrode needle.

The ejection orifice(s) may open out radially.

For a flattened electrode needle in particular, the injection channel 36 may be defined, at least partially, by a wall in a non metallic material, in particular a polymer, for example chosen in the group formed of polymers of silicone, polyester, polyorthoester, polymethyl methacrylate and any other flexible medical-grade polymers. The injection channel 36 is preferably defined by a wall made in silicone.

Preferably, according to the embodiment of FIG. 4, the device comprises only one single injection needle 42, preferably provided with a needle stop to limit the insertion into the eye.

Guidance of the Needles

The support 16 may be provided with one or a plurality of insertion guides 28.

A needle, i.e. an electrode needle 14 or an injection needle 42, can therefore be mobile and guided between an extreme (i.e. limited by an abutment) close position and a remote position in which it is protruding and not protruding, respectively, inside from the support contact surface 18. The device may comprise a mechanism to automatically change the position of a needle, and in particular of an electrode needle 14, from the remote position to the close position.

The guided movement of a needle may be in rotation and/or in translation.

Preferably, an insertion guide 28 is configured so as to hinder any rotation of the corresponding needle around its longitudinal axis. As represented in FIG. 2a, the cross section of an insertion guide 28 may be asymmetric and complementary to that of the corresponding needle, e.g. rectangular as represented.

In an embodiment, the guidance results from the contact between the inserted needle and the surface of the hole of the support into which the needle is inserted, as represented in FIG. 4.

The support preferably comprises an electrode insertion guide 28a to guide, by contact with an invasive electrode needle, the insertion of an invasive electrode needle, and/or an injection needle insertion guide 28b to guide, by contact with an injection needle, the insertion of said injection needle.

The cross-section of an insertion guide 28a or 28b preferably matches the cross-section of the corresponding electrode needle or injection needle, respectively.

Preferably, an insertion guide 28a or 28b has the shape of a hole which goes through the support, exiting on its contact and outside surfaces through corresponding outlet orifice 30 and inlet orifice 32, respectively.

The largest and/or the smallest dimension(s) of the cross-section of the hole is preferably less than 0.5 mm, preferably less than 0.4 mm, preferably less than 0.35 mm, and/or preferably greater than 0.2 mm, preferably greater than 0.3 mm.

Preferably, the hole has a shape of a tube, having preferably a constant cross-section along its length. The length of an insertion guide is preferably greater than 0.5 mm, preferably greater than 1 mm, preferably greater than 2 mm.

The cross-section is preferably circular.

Alternatively or in addition, in a preferred embodiment, the first electrode and/or the injection needle comprises at least one, preferably at least two guiding rods 39, extending parallel to the electrode needle(s) and/or to the injection needle, respectively, and the support comprises corresponding rod insertion guides 28c (see FIG. 5g).

The length $l_{39}$ of a guiding rod is preferably greater than 12 mm, preferably greater than 14 mm, and/or less than 20 mm, preferably less than 17 mm, preferably less than 16 mm.

Preferably, the rod insertion guides 28c are holes which do not penetrate into the virtual sphere S on which the support contact surface 18 extends. Therefore, when the support contact surface 18 bears on the outside surface of an eye O, the guiding rods cannot go through the support contact surface 18, and consequently cannot penetrate into the eye. Advantageously, the guiding length, i.e. the length of the insertion guide 28c can be increased.

Preferably, a guiding rod, or any guiding rod is provided with a rod stop 40 that is able to limit the sliding movement of said guiding rod 39 outside the corresponding rod insertion guide 28c, as represented in FIG. 6c. In this figure, the rod stop 40 abuts on the support 16, in particular in the bottom of a sliding rail 41.

Preferably, only one guiding rod is provided with a rod stop 40.

Preferably, only one guiding rod is provided for the set of all the rod stops 40.

Preferably, the sliding of the rod stop 40 in the support is not guided.

The guiding rod 39 is therefore mobile from a retracted position (FIGS. 6a and 6c) and an inserted position (FIGS. 6g and 6h), wherein the needle(s) guided by the guiding rod 39, i.e. the four electrode needles in the embodiment of FIG. 6, is (are) outside the virtual sphere S (see FIG. 6a) and at least partly inside the virtual sphere S (see FIG. 6g), respectively.

In the retracted position, the support contact surface can advantageously be placed so as to bear on the eye, before the insertion of the guided needle(s), without any risk of injury.

Advantageously, a rod stop 40 hinders the dismounting of the corresponding guiding rod 39 from the support. In any position, and in particular in the retracted position, the guiding rod is therefore always at least partly inside the corresponding rod insertion guide. Consequently, for the insertion of the guided needle(s) into the eye, there is no need for any previous introduction of a guiding rod into a corresponding rod insertion guide. The insertion of the guided needle(s) is therefore made easier.

In addition, there is no risk that the tip of said guided needle(s) could touch the support, and possibly extract some part of the support and introduce it into the eye. Alternatively or in addition, for the same purpose, an insertion guide, and in particular an injection needle insertion guide 28b, may be defined with a metal or a ceramic material. A metal or ceramic cover may be provided on the support or the insertion guide may be defined with a metal or ceramic tube or part 43 (see FIG. 6g).

Preferably, as represented in FIG. 6a, the tip 27 of (a) guided needle(s) is (are) inside the support in the retracted position of the guiding rod. Advantageously, the risk of injury is therefore limited.

Preferably, the guiding rod(s) of the first electrode and/or the injection needle extends beyond the tip of the electrode needle(s) of the first electrode and/or of the injection needle, respectively, by a distance $\Delta_{39}$ which is preferably greater than 1 mm, preferably greater than 2 mm, preferably greater than 3 mm, and/or preferably less than 8 mm, preferably less than 7 mm, preferably less than 5 mm, preferably less than 4 mm.

Advantageously, the guiding rods may be inserted in their respective rod insertion guides 28c before any penetration of an electrode needle of the first electrode and/or of the injection needle, respectively, into the corresponding insertion guide 28a or 28b of the support. Therefore the tip of the inserted needle may not prick into the inner surface of said insertion guide 28a or 28b.

Preferably, the largest transversal dimension $e_{39}$ of a guiding rod 39, i.e. in a cross-section perpendicular to its length, is greater than 0.5 mm, preferably greater than 0.8 mm, preferably greater than 0.9 mm, and/or less than 2.0 mm, preferably less than 1.5 mm, preferably less than 1.2 mm. Advantageously, the rigidity of the guiding rod is increased and guidance is improved.

Preferably, the device comprises a needle stop, generally referenced as 29, that is able to limit the movement of the electrode needle 14, referenced as 29a, and/or of an injection needle, referenced as 29b, and/or of a guiding rod 39, referenced as 29c, during the stage of penetration into the eye.

In the close position represented in FIG. 3a, the needle stop 29 abuts on the support 16 so as to define the insertion length of the needle into the eye O.

A guiding rod stop 29c is preferably rigidly fixed on the guiding rod(s) 39, as represented on FIG. 6c.

The length of the part of an electrode needle and/or of an injection needle which may be inserted (insertion length) in the eye is determined so that the tip of said electrode needle and/or injection needle may not reach the region of the virtual sphere which is opposite to the insertion point of said needle.

Preferably, a needle stop 29a (or 29c if an electrode needle is guided by a guiding rod, as in FIG. 6) is configured so that in a front view of the second electrode, i.e. when observing the second electrode along its main axis, the inserted electrode needle(s) extend, in a close position, so as to completely cross the electrode contact surface defined by the second electrode (i.e. extend in front of the electrode contact surface at least from one side to the opposite side of the electrode contact surface).

A needle stop 29 preferably comprises wings 45 to make the handling of the needle stop easier (see FIG. 6c).

A needle stop 29a preferably comprise connectors 46 for the electrical connection to a terminal of the generator. A connector 46 may comprise a screw to press a wire electrically connected to said terminal on a part electrically connected to the electrode needle(s). It may also comprise a socket electrically connected to the electrode needle(s) and configured to cooperate with a corresponding plug of a wire electrically connected to said terminal, such as a micro jack plug.

An insertion guide and the corresponding needle are preferably configured so that, in the close position, the needle can only penetrate at a maximal depth, measured from the surface of the virtual sphere.

Preferably, the maximal depth $p_{42}$ for any injection needle is greater than 0.6 mm, preferably greater than 0.7 mm, preferably greater than 0.8 mm, and/or less than 1.2 mm, preferably less than 1.1 mm, preferably less than 1.0 mm (See FIG. 6e).

Preferably, the maximal depth $p_{14}$ for an electrode needle, preferably for any electrode needle is greater than 1.3 mm, preferably greater than 1.4 mm, preferably greater than 1.5 mm, preferably greater than 1.6 mm, and/or less than 2.1 mm, preferably less than 1.9 mm, preferably less than 1.8 mm, preferably less than 1.7 mm (See FIG. 6e).

In an embodiment, the support is configured so that, in the close position, the depth of the tip 27 of an electrode needle and/or an injection needle under the virtual sphere S defining the support contact surface 18 is the same, independently from the insertion guide 28a and/or 28b, respectively, into which said electrode needle and/or injection needle is introduced.

In an embodiment, the support is configured so that, in the close position, the position of the tip 27 of an electrode needle and/or an injection needle, and in particular the insertion depth of the needle, depends on the insertion guide 28a and/or 28b, respectively, into which said needle is introduced.

Advantageously, the support may therefore be locally adapted to define different insertion lengths and/or different orientations of the insertion guides 28a or 28b, as represented in FIG. 3a'.

A plurality of insertion guides may be used to enable different close positions for a needle and/or to provide a single close position for a first electrode or for injection means comprising several needles.

In particular, when the support comprises several electrode insertion guides 28a, possibly with different lengths or orientations, the insertion of corresponding electrode needles makes it possible achieving an optimal net of electrode needles.

If the electrode needle 14 is also an injection needle, this multiplicity of different insertion guides advantageously allows for a plurality of injections at different points so as to very precisely define the region into which the product is to be injected. Advantageously, the region of the eye that an injection needle may reach is also enlarged.

Finally, this multiplicity of different insertion guides advantageously allows for the same support to be used for different applications or different products.

The insertion guides are preferably rectilinear.

In an embodiment, the insertion guides 28a and/or 28b and/or 28c are all parallel to each other.

In an embodiment, which is not preferred, when observed along the axis X, the insertion guide(s) 28, i.e. 28a and/or 28b and/or 28c extend(s) substantially radially relatively to said rim (i.e. in a plane containing the axis X, see the middle guide in FIG. 2b), and in particular extends along an insertion axis $\Delta_{28}$ which makes, with a direction tangential to said rim and containing the point of intersection of the insertion axis and of the rim 20, an angle $\theta_{28}$, greater than 60°, greater than 70° and/or less than 110°, less than 100°. In particular, an insertion guide may extend substantially in a plane containing the centre C of the spherical virtual sphere S and perpendicular to the circular rim 20, as represented in FIG. 3a.

Preferably, the angle $\theta_{28}$ is less than 45°, preferably less than 30°, preferably less than 20°, preferably less than 10°.

Preferably, an insertion guide, preferably any insertion guide extends along an insertion axis $\Delta_{28}$ which defines an angle β less than 20°, less than 15°, less than 10°, less than 5°, less than 1° with a plane $P_{20}$ containing said rim.

Preferably, an insertion guide, preferably any insertion guide extends parallel to the plane $P_{20}$.

Preferably, at least one electrode insertion guide 28a, preferably at least the electrode insertion guide 28a which is the closest to the plane $P_{20}$ of the rim 20, is conformed so that, in the close position, an electrode needle 14 inserted in said electrode insertion guide 28a extends at a distance d greater than 2 mm, preferably greater than 3 mm, preferably greater than 3.5 mm, preferably greater than 4 mm, and less than 6 mm, preferably less than 5 mm, less than 4.5 mm, from the plane $P_{20}$ of the rim 20 (i.e. the distance d applies to any point of the electrode needle (See FIG. 4e)).

Preferably, at least one, preferably any electrode insertion guide 28a, is conformed so that, in the close position, an electrode needle 14 inserted in said electrode insertion guide 28a completely extends outside the virtual cylinder Cy of axis X bearing on said rim (see FIG. 3a').

Preferably, at least one, preferably any electrode insertion guide 28a, is conformed so that, in the close position, the non insulated part 14b of an electrode needle 14 inserted in said electrode insertion guide 28a extends, when observed along the axis X, at least partially, preferably completely within the area in front of the second electrode.

When the electrode contact surface is rectangular, the insertion axis of an insertion guide, preferably of any insertion guide is preferably substantially parallel to one of the sides, preferably a large side, of the electrode contact surface.

In the case where the electrode needles are coplanar, the plane of the electrode insertion guides is preferably substantially parallel to the large and/or small sides.

Preferably, an insertion guide 28, preferably any insertion guide 28 extends substantially parallel to the general plane $P_{17}$ of the electrode contact surface 17 of the second electrode.

Preferably, the insertion axis $\Delta_{28}$ of an insertion guide 28, preferably of any insertion guide, defines an angle with a plane perpendicular to the main axis $\Delta_{17}$ of the electrode contact surface 17, being less than 50°, less than 30°, less than 20°, less than 10°, preferably less than 5°, preferably substantially null, as represented in FIG. 4e.

Preferably, when the electrode contact surface is spherical, at least a radius of said electrode contact surface 17 is included in a plane perpendicular to said insertion axis. Preferably, said radius crosses said electrode contact surface about its centre.

Preferably, the electrode insertion guides 28 are configured so that, in the close position, the distance δ between the invasive electrode needle 14, preferably any invasive electrode needle, and the electrode contact surface 17 is between 2.0 and 1.3 mm, preferably between 1.8 and 1.5 mm, preferably between 1.7 and 1. mm, preferably about 1.65 mm, and preferably is substantially constant whichever point of the electrode contact surface is being considered, as represented in FIG. 1b or FIG. 4e.

Preferably, at least two electrode insertion guides 28a extend in a common plane $P_{28a}$. In a preferred embodiment, all the electrode insertion guides 28a extend in the same plane $P_{28a}$. Preferably, as represented in FIG. 4e, the plane $P_{28a}$ defines with the plane $P_{20}$ of the rim 20 an angle Ω which is greater than 40°, greater than 45°, preferably greater than 50°, and/or less than 80°, preferably less than 70°, preferably less than 60°, preferably less than 55°.

In an embodiment, the outlet orifices 30 and/or inlet orifices 32 of the electrode insertion guides 28a do not all extend at the same distance from the plane $P_{20}$ of the rim 20, as represented in FIG. 3a or FIG. 4e.

Preferably, the plane $P_{28a}$ extends substantially parallel to the electrode contact surface which is intended to come into contact with the outside surface of the eye. The angle between said plane $P_{28}$ and the general plane in which the second electrode extends (plane perpendicular to the main axis of the second electrode), is preferably less than 20°, preferably less than 15°, preferably less than 10° or less than 5°.

Preferably, all the invasive electrode needles of the first electrode, preferably three, preferably four electrode needles, extend, in the service position, in the plane $P_{28a}$. Preferably, at any point of the electrode contact surface 17 of the second electrode, the distance δ between the electrode contact surface 17 and the plane $P_{28}$ is between 2.0 and 1.3 mm, preferably between 1.8 and 1.5 mm, preferably between 1.7 and 1. mm, and is substantially constant whichever point of the electrode contact surface is being considered (see FIG. 4*e*).

The injection needle insertion guide(s) may have one or several characteristics of the electrode insertion guides 28*a*.

In an embodiment, the support comprises at least one, preferably a plurality of electrode insertion guides 28*a* and at least one injection needle insertion guide 28*b* configured to guide the insertion into the eye of electrode needle(s) and injection needle(s) along respective insertion axis, wherein planes perpendicular to said respective insertion axis define an angle greater than 3°, greater than 5°, and/or less than 10°. In other words, in the close position, the electrode and injection needles are not inserted parallelly to each other. Advantageously, the electrode contact surface 17 of the second electrode can be enlarged, without any deterioration of the mechanical resistance of the support.

The support preferably comprises prepositioning guide(s) configured to guide one or several needles, i.e. electrode needle(s) and/or injection needle(s), into a position wherein said electrode needle(s) and/or injection needle(s) is(are) in line with the axis of a corresponding insertion guide.

Advantageously, the prepositioning of a needle allows for an alignment of this needle with a corresponding insertion guide, so that during the insertion, the tip of the needle will not contact the support and therefore will not be blunted.

In particular, the support preferably defines prepositioning means which makes the insertion of the needle(s) into the inlet orifice(s) 32 easier.

Preferably, as represented in FIG. 4*e*, the prepositioning means comprise a converging chute 33. The chute 33 comprises a large opening 34 in which it is easy introducing the needle. The converging part of the chute 33 guides the needle until it reaches the bottom of the chute 33. At this position, the tip of the needle faces an inlet orifice 32 so that it may be introduced into the inlet orifice without any risk of hitting the support when it is introduced into the inlet orifice 32.

In the embodiment of FIG. 4*e*, it is however necessary that the three electrode needles bear an inclined surface 35 of the chute 33.

Similar insertion guides and prepositioning means can be provided for the electrode needle(s) and for the injection needle(s). In particular, as represented in FIGS. 4*b* and 5*b*, a chute 44 may be provided so that an injection needle be aligned with an inlet orifice of an injection needle insertion guide 28*b*.

The embodiment of FIG. 5 does not comprise a chute for the electrode needles, because of the guidance by the guiding rods 39 into the rod insertion guides 28*c*.

Pharmaceutical Composition

The injected product may be, in particular, any of the pharmaceutical compositions described in WO/2013/024436, incorporated by reference, and in particular a therapeutic nucleic acid of interest, preferably a desoxyribonucleic acid (DNA) molecule (cDNA, gDNA, synthetic DNA, artificial DNA, recombinant DNA, etc.) or a ribonucleic acid (RNA) molecule (mRNA, tRNA, RNAi, RNAsi, catalytic RNA, antisens RNA, viral RNA, etc.). In an embodiment, the composition contains a circular piece of DNA.

In another particular embodiment, the electroporation device of the invention is particularly suitable for performing gene replacement. Accordingly the nucleic acid may encode for a viable protein so as to replace the defective protein which is naturally expressed in the targeted tissue. Typically, defective genes that may be replaced include, but are not limited to, genes that are responsible for the diseases disclosed in WO/2013/024436.

Kit

In accordance with the present invention, kits are envisioned. A device according to the invention and a pharmaceutical composition according to the invention, and optionally instructions for use may be supplied together in a kit. Within the kit, the components may be separately packaged or contained.

Instructions can be in written, video, or audio form, and can be contained on paper, an electronic medium, or even as a reference to another source, such as a website or reference manual.

Other components such as excipients, carriers, other drugs or adjuvants, instructions for administration of the active substance or composition, and administration or injection devices can be supplied in the kit as well.

Method

The method of the invention may be used for treating an ocular disease in a subject, the pharmaceutical composition being preferably chosen among the pharmaceutical compositions which are described here above.

To use the electroporation device according to the first aspect of the invention, an operator may proceed by the following steps:

First, the operator fixes the second electrode on the support, couples a reservoir filled with the pharmaceutical composition to the injection needle, and electrically connects the first and second connectors to the two terminals of the electrical generator.

To position the device, the operator places the rim 20 on the limbus Li of the eye O. The placement of the rim 20 on the edge of the cornea and the bearing of the spherical support contact surface 18 on the sclera guarantee a good stability of the device and a very precise positioning. The stabilisation is very important in the present specific application, since the angles between the electrode needles and/or injection needle in one hand, and the spherical support contact surface in the other hand, are very low at the insertion points, i.e. the needles are inserted almost tangentially to this surface, which makes the insertion difficult.

The operator then pushes the first electrode, preferably a comb of electrode needles, previously in a remote position, into the insertion guides 28*a*.

In an embodiment, the guiding rods 39 penetrate into the corresponding rod insertion guides 28*c*. In another embodiment, the guiding rods are slidably mounted on the support, and maintained on the support with one or several rod stops, so that, advantageously, no insertion of a guiding rod 39 into the corresponding rod insertion guide is necessary.

They can then guide the movement of the first electrode, to make sure that the electrode needles easily enter into their corresponding insertion guides 28*a*, until the first electrode abuts on the outside surface 26 of the support 16, and therefore reaches the close position. The electrode needles then define a grid which extends substantially parallel to the second electrode, all along the length of the second electrode.

The inventors have shown that human eyes all have very similar dimensions and shapes and, in particular, that the distance between the ciliary muscle and the edge of the cornea of an eye is substantially the same regardless of the individual concerned. The shape and arrangement of the first electrode and of the second electrode, of the insertion guides 28, of the pikes 26, of the rim 20, and of the spherical contact surface are determined such that, in the close position, the operator is guaranteed that the first and second electrodes are in the optimal position to create an electrical field particularly effective for electroporation into the ciliary muscle.

The operator then inserts the injection needle in the corresponding insertion guide, until a corresponding close position. The previous insertion of the electrode needles enables a very stable position of the support during the insertion of the injection needle.

In an embodiment, the stop of the injection needle determining its close position is determined for the ejection orifice(s) to open in the ciliary muscle, in front of the grid of the electrode needles.

The operator can then inject the composition.

In a preferred embodiment, the injection needle is part of a syringe and the operator put the injection needle in the chute 44 so that it faces the inlet orifice of the injection needle insertion guide. The operator then inserts the injection needle through the injection needle insertion guide 28b, in the space between the first and second electrodes, injects the composition and then withdraws the injection needle from the eye.

Multiplication of the injection points promotes the penetration of the composition.

The device is then in the service position and the operator sends a suitable electrical signal, for example suitable electrical impulses, by means of the electrical generator, in such a way as to create, within the injection zone, an electrical field that promotes electroporation. The above described configuration of the device, and in particular with a flattened shape for the electrode needle(s), improves the electroporation efficiency.

In a particular embodiment, an electrical field constituted by one or more electrical pulse(s) is applied.

The field intensity of which is preferably between about 1 and 600 Volts, preferably 1 and 400 Volts, even more preferably between about 1 and 200 Volts, advantageously between about 10 and 100 Volts, or 15 and 70 Volts.

The total duration of application of the electric field may be between 0.01 millisecond and 1 second, preferably between 0.01 and 500 milliseconds, more preferably between 1 and 500 milliseconds, even more preferably greater than 1 or 10 milliseconds. In a preferred embodiment, the total duration of application of the electric field is between 10 milliseconds and 100 milliseconds and is preferably of 20 milliseconds.

The number of electric pulses applied may be between for example 1 and 100 000. Their frequency may be comprised between 0.1 and 1000 Hertz. It is preferably a regular frequency.

Electric pulses may also be delivered in an irregular manner relative to each other, the function describing the intensity of the electric field as a function of the time for one pulse being preferably variable.

Electric pulses may be unipolar or bipolar wave pulses. They may be selected for example from square wave pulses, exponentially decreasing wave pulses, oscillating unipolar wave pulses of limited duration, oscillating bipolar wave pulses of limited duration, or other wave forms. Preferentially, electric pulses comprise square wave pulses or oscillating bipolar wave pulses.

When the electroporation of the product has been completed, the operator electrically disconnects the electrodes and the generator.

As will now be clear, the device according to the invention permits
 precise and stable positioning of the electrodes;
 precise guidance of the invasive electrode needle during its penetration into the eye;
 precise injection into the eye relative to the limbus;
 the generation of an efficient homogeneous large electrical field.

Of course, the invention is not limited to the embodiments described and shown, which have been provided by way of illustration.

In particular, the various embodiments could be combined.

The invention claimed is:

1. An electroporation device for injecting a product into a ciliary muscle of an eye, said device comprising:
 a support having a spherical support contact surface extending along a virtual sphere, the virtual sphere having a radius between 10 and 15 mm,
 a first electrode comprising an invasive electrode needle,
 a second electrode having an electrically conductive electrode contact surface,
 an injection needle,
 wherein the support comprises a rectilinear insertion guide extending along an axis, called "insertion axis", defining an angle less than 40° with a plane tangential to the virtual sphere at a point where said insertion axis crosses said virtual sphere, called "insertion point".

2. An electroporation device according to claim 1, wherein said angle is less than 30°.

3. An electroporation device according to claim 1, wherein the angle is less than 25°.

4. An electroporation device according to claim 1, wherein the angle between said insertion axis and a plane perpendicular to a main axis of the electrode contact surface is less than 5°, the "main axis" of the electrode contact surface being the direction perpendicular to said surface passing through a center of said electrode contact surface.

5. An electroporation device according to claim 1, wherein the support comprises at least two electrode insertion guides, which extend in a common plane which defines, with a plane perpendicular to the main axis of the electrode contact surface an angle less than 5°.

6. An electroporation device according to claim 1, wherein the support defines a circular rim, having an axis X and a radius of greater than 5 mm and of less than 8 mm, so as to match the limbus of an eye, wherein the insertion axis defines, at the insertion point, an angle less than 40° with a plane tangential to a cylindrical surface of axis X containing the insertion point and having a circular base.

7. An electroporation device according to claim 1, wherein the support defines a circular rim, having an axis X and a radius of greater than 5 mm and of less than 8 mm, so as to match the limbus of an eye, wherein an insertion guide extends along an insertion axis which defines an angle β less than 20° with a plane containing said rim.

8. An electroporation device according to claim 7, wherein the support comprises at least two electrode insertion guides, all the electrode insertion guides extending parallel to each other in a common plane which defines with the plane of the rim an angle Ω which is greater than 40° and less than 80°.

9. An electroporation device according to claim 7, wherein said rim is interrupted by at least one notch located in a portion of the rim which extends along an angular sector less than 120° and centred on a median plane of the second electrode.

10. An electroporation device according to claim 1, wherein the insertion guide is configured so that, in a position corresponding to a full insertion of said electrode needle, the distance between the electrode needle and the electrode contact surface is between 2.0 and 1.3 mm, and is substantially constant whichever point of the electrode needle is being considered.

11. An electroporation device according to claim 1, wherein a length of said electrode needle is determined so that, when observing the second electrode along a direction perpendicular to said second electrode and passing through its centre, the electrode needle extends, in a position corresponding to a full insertion of said electrode needle, so as to completely cross the electrode contact surface.

12. An electroporation device according to claim 1, wherein a surface area of the electrode contact surface is greater than 6 mm$^2$ and less than 20 mm$^2$.

13. An electroporation device according to claim 1, wherein the electrode contact surface extends on the same virtual sphere as the support contact surface.

14. An electroporation device according to claim 1, wherein the first electrode and/or the injection needle comprises at least one guiding rod, extending parallel to the electrode needle(s) and/or to the injection needle, respectively, and the support comprises corresponding rod insertion guide(s).

15. An electroporation device according to claim 14, wherein the insertion guide(s) is(are) holes which do not cross the virtual sphere on which the support contact surface extends.

16. An electroporation device according to claim 14, wherein the guiding rod(s) of the first electrode and/or the injection needle is provided with a rod stop that is able to limit the sliding movement of said guiding rod outside the corresponding rod insertion guide.

17. An electroporation device according to claim 15, wherein the guiding rod(s) of the first electrode and/or the injection needle extends beyond the tip of the electrode needle(s) of the first electrode and/or of the injection needle, respectively, by a distance which is greater than 3 mm.

18. An electroporation device according to claim 16, wherein the largest transversal dimension of a guiding rod is greater than 0.5 mm.

19. An electroporation device according to claim 1, wherein the support comprises prepositioning guide(s) configured to guide an electrode needle and/or an injection needle into a position wherein said electrode needle and/or said injection needle is(are) in line with an axis of a corresponding insertion guide.

20. An electroporation device according to claim 1, comprising
an electrode insertion guide and an injection needle insertion guide configured to guide a sliding of said electrode needle and injection needle along respective electrode needle insertion axis and injection needle insertion axis, any plane perpendicular to said electrode needle insertion axis being parallel to any plane perpendicular to said injection needle insertion axis.

21. An electroporation device according to claim 1, wherein, in a position corresponding to a full insertion of the injection needle, a maximal depth of the injection needle under the virtual sphere is between 0.8 mm and 1.0 mm, and wherein, in a position corresponding to a full insertion of the electrode needle, the maximal depth of the electrode needle under the virtual sphere is between 1.5 mm and 1.8 mm.

22. An electroporation device according to claim 1, comprising a reservoir containing said product and an injection needle in fluid communication with said reservoir, said product being a therapeutic nucleic acid of interest.

23. An electroporation device according to claim 22, wherein the product is a desoxyribonucleic acid molecule or a ribonucleic acid molecule.

24. An electroporation device according to claim 7, wherein the insertion guide extends along an insertion axis which defines an angle β less than 10° with a plane containing said rim.

25. An electroporation device according to claim 7, wherein the insertion guide extends along an insertion axis which defines an angle β less than 1° with a plane containing said rim.

26. An electroporation device according to claim 8, wherein the common plane defines with the plane of the rim an angle Ω which is greater than 45°, and less than 70°.

27. An electroporation device according to claim 8, wherein the common plane defines with the plane of the rim an angle Ω which is greater than 50° and less than 60°.

28. An electroporation device according to claim 5, wherein the at least two electrode insertion guides are parallel to each other.

* * * * *